United States Patent [19]

Vertesy et al.

[11] 4,204,058

[45] May 20, 1980

[54] PROCESS FOR OBTAINING CEPHALOSPORIN C AND THE SALTS AND DERIVATIVES THEREOF FROM CULTURE FILTRATES OR CULTURE SOLUTIONS

[75] Inventors: Laszlo Vértesy, Eppstein; Gerhard Huber, Kelkheim, both of Fed. Rep. of Germany

[73] Assignee: Hoechst Aktiengesellschaft, Frankfurt, Fed. Rep. of Germany

[21] Appl. No.: 954,896

[22] Filed: Oct. 26, 1978

[30] Foreign Application Priority Data

Oct. 29, 1977 [DE] Fed. Rep. of Germany ....... 2748659

[51] Int. Cl.$^2$ ............................................ C07D 501/12
[52] U.S. Cl. ........................................... 544/4; 544/20
[58] Field of Search ...................... 544/20, 4

[56] References Cited

U.S. PATENT DOCUMENTS 3,983,109  9/1976  Oppici et al. .......................... 544/20

*Primary Examiner*—Nicholas S. Rizzo
*Attorney, Agent, or Firm*—Curtis, Morris & Safford

[57] ABSTRACT

A novel process for obtaining cephalosporin C and the salts and derivatives thereof from culture filtrates or culture solutions is provided which comprises drying the culture filtrate or culture solution, dissolving it in an optionally water-containing solvent different from water, and
(a) forming a derivative of the amino group of cephalosporin C, and isolating it in the form of a free acid or a salt, or
(b) precipitating the cephalosporin C or the scarcely soluble salt thereof directly.

20 Claims, No Drawings

PROCESS FOR OBTAINING CEPHALOSPORIN C AND THE SALTS AND DERIVATIVES THEREOF FROM CULTURE FILTRATES OR CULTURE SOLUTIONS

The present invention relates to a process for obtaining cephalosporin C and the salts and derivatives thereof from culture filtrates or culture solutions by contacting optionally water-containing solvents different from water with the culture media in a dried state, and optionally further chemical reactions.

Cephalosporin C is an interesting antibiotic from which the most diverse medicaments can be prepared by chemical reactions. It is formed by growing special microorganisms such as *Cephalosporium acremonium*.

In the culture fluids of these microorganisms, cephalosporin C is present as well as many other products of metabolism. Generally, cephalosporin C must be isolated from the fermentation mixture before further use. Various corresponding processes have been described hitherto. Cephalosporin C can be purified, for example, by ion exchange (see German Offenlegungsschrift No. 1,492,049) or by precipitation with salts of heavy metals (see German Offenlegungsschrift No. 1,966,849). Furthermore, the relatively polar, hybrid ion antibiotic, which cannot be extracted with water-immiscible solvents, can be converted by chemical reactions to a nonpolar form. Thus, cephalosporin C can be extracted with certain water-immiscible solvents, for example butanol or methylisobutylketone, from an aqueous solution, and isolated. As suitable reactions, there have been proposed, for example, conversion of the free amino group or the free carboxylic groups of cephalosporin C (see for example U.S. Pat. No. 3,234,223). All these reactions proceed in a satisfactory manner only in the case where the aqueous solutions contain pure cephalosporin C. However, the filtrates obtained from the fermentation solutions contain numerous impurities, for example fats, salts, albuminous substances or polysaccharides, which considerably disturb the cited purification processes. The conversion of cephalosporin C to derivatives capable of being extracted gives yields of less than 50% only, while yields of more than 90% are obtained under identical conditions when aqueous solutions of pure cephalosporin C are used. Therefore, proposals have been made to purify efficiently the cephalosporin C before the cited separation operations [see for example J. Appl. Chem. Biotechn. 26. 459-468(1976)], which purification may be carried out by adding a 2- to 3-fold amount of acetone. Thus, part of the impurities becomes insoluble and can be removed by filtration. However, the fact that very large amounts of acetone are required for the large-scale fermentations which are usual in industrial practice prevents this method from becoming commonly used. Moreover, part of the cephalosporin C is carried along with the impurities removed, thus reducing the yield.

Another method of prepurification consists in employing adsorption resins according to the specification of German Offenlegungsschrift No. 2,021,696. However, since in this case considerable amounts of an expensive resin have to be used and large volumes of water and aqueous organic solvents are required for the treatment of this resin, which may amount to a multiple of the fermentation volume, the use of such resins is no optimum solution of the problem either. A further disadvantageous factor is the considerable expenditure for apparatus in this method.

The process of the invention overcomes these difficulties in the following manner: the culture filtrate or the culture solution containing the intended antibiotic is first dried, and the dried product is then dissolved in an optionally water-containing solvent different from water. In view of the state of the art, it was surprising to observe that in the solutions so obtained chemical reactions of cephalosporin C to form the derivatives or insoluble salts thereof can be carried out with very good yields. Subsequently, these derivatives can be either precipitated directly from the organic solvent, or distributed between water and a water-immisible solvent and then precipitated from the separated organic phase by means of a suitable additive, for example and especially advantageously, a diamine. When an insoluble salt is so formed in the solvent differing from water, it can easily be filtered off.

The present invention therefore provides a process for obtaining cephalosporin C, the salts and derivatives thereof from culture filtrates or culture solutions, which process comprises drying the culture filtrate or the culture solution, dissolving it in an optionally water-containing solvent different from water, and (a) forming a derivative of the amino group of cephalosporin C, and isolating the derivative in the form of a free acid or a salt, or (b) precipitating cephalosporin C or a scarcely soluble salt thereof directly from the solvent different from water.

The culture filtrate or culture solution can be dried according to suitable known processes, for example lyophilization, spray drying or distillation processes such as especially, vacuum distillation, with the proviso that the temperatures used are not too high, in order to prevent complete or partial inactivation of the antibiotic, which is sensitive to heat. Because of its simple and cheap operational mode, spray drying will be generally preferred in accordance with this invention. The culture solution or culture filtrate can be dried either directly or after previous alteration of the pH, which latter adjustment may be advantageous especially in the case where part of the impurities can be precipitated by moderate acidification only. However, the liquid to be dried soluble be of such a nature that, on corresponding concentration, no extreme pH values occur, for example below 2 or above 9. Preferably, operations are carried out at a pH from about 4 to about 7. The drying processes give products which may contain a certain residual moisture, the amount of which may widely vary, generally from about 0.1 to 50%. Usually, from 2 to 12% of residual moisture are present.

In principle, the cephalosporin C can be extracted from the dried culture filtrate or culture solution by means of any solvent different from water in which the cephalosporin is sufficiently soluble. In the case where such a solvent is used without the addition of water, formamide for example is suitable, but glacial acetic acid is preferred.

Anhydrous extraction is not required; on the contrary, a small amount of water, which may be for example from 3 to 30%, depending on the solvent used, increases the dissolving power of many solvents in such a manner that they can be used for extracting cephalosporin C. On the other hand, too high a water content, for example above 30%, reduces the good reactivity of cephalosporin C. Suitable solvents to be used, preferably with a certain, water content are for example acetonitrile, dimethyl formamide, low molecular weight aliphatic alcohols, preferably methanol, or methyl cellosolve, phenol, pyridine, trimethyl phosphate, or mixtures of these solvents. Of course, these solvents can be mixed with solvents usually employed in anhydrous form, such as glacial acetic acid or formamide, or with other additives increasing the dissolving power. When water-containing solvents are used, methanol containing from about 5 to about 30%, especially 5 to 15%, preferably 10%, of water has proved to be suitable.

When extracting the dried culture filtrate or culture solution, it may dissolve either completely or partially in the solvent. The essential criterion of the solvent, however, is an optimum dissolving power for cephalosporin C. The extent of solubility of the dry matter depends above all on the nutrient used, and the good reactivity in accordance with the invention of the cephalosporin C solutions formed by the extraction is not adversely affected thereby.

The cephalosporin C can be further isolated from the extracts of dry matter according to diverse methods. For example, it may be obtained from the solution by direct precipitation. While cephalosporin C can be precipitated from aqueous solutions with difficulty only, this precipitation occurs smoothly in the solvents different from water used in accordance with this invention.

Especially suitable, for precipitation are for example inorganic ions of heavy metals forming an insoluble salt with cephalosporin C, such as bivalent cobalt, copper, tin or zinc ions, organic gases such as, for example acridine or rivanol, or non-polar solvents such as acetone, low molecular weight alcohols especially those having from 3 to 6 carbon atoms, for example n-propanol, butanols such as n-butanol or isobutanol, and amyl alcohols or ethyl acetate. When the solutions contain many impurities, that is, when the solids content is about 8% or more, the precipitate, too, may still be impure. In these cases, it is advantageous to carry out a preliminary precipitation which removes the substantial part of the impurities from the solution, but not the cephalosporin C. For this preliminary precipitation, known precipitation agents can be used, for example tannin, phosphotungstic acid, flavianic acid, potassium bismuth or rivanol. The cephalosporin is separated nearly completely from the supernatant of the preliminary precipitation by means of one of the above precipitating agents, for example zinc acetate.

Another method of isolating the cephalosporin from the extract of the dry culture solution or culture filtrate is based on the observation that in the solvents different from water used in accordance with this invention the free amino group of cephalosporin C can be easily converted without any difficulty to derivatives known per se. The corresponding derivatives are formed also when the carboxyl group is reacted. In this case, compounds having no hybrid ion structure are obtained.

According to this method, reactions of the amino group with acid halides, preferably acid chlorides, such as benzoyl chloride or chloroformic acid benzyl ester, to form acyl derivatives proceed especially smoothly. These reactions may be carried out in a manner which is usual in such cases. Alternatively, other acid halides, preferably chlorides, may be used, for example those of optionally substituted aliphatic carboxylic acids having from 2 to 18 carbon atoms, such as acetyl chloride, acetyl bromide, chloroacetyl chloride, propionyl chloride, n-butyryl chloride, n-valeryl chloride, isovaleryl chloride, capryl chloride, n-lauryl chloride, n-palmityl chloride, n-stearyl chloride; or those of optionally substituted aromatic carboxylic acids such as benzoyl bromide, mono-, di- or trichlorobenzoyl chlorides, or mono-, di- or trinitrobenzoyl chlorides; of those of optionally substituted sulfonic acids such as benzoylsulfonyl chloride or the alkyl derivatives thereof such as toluenesulfonyl chloride, or naphthylsulfonyl chloride and the derivatives thereof. When the operations are to be carried out under gentle conditions, the acid anhydrides which react more slowly as reactant and acylation agent, for example acetic anhydride, may alternatively be used in corresponding solvents. Also in this case, other aliphatic or aromatic acid anhydrides may be employed, for example anhydrides of fatty acids having from 2 to 18 carbon atoms, such as propionic, butyric, n-valeric, isovaleric, n-caproic or isocaproic acid; anhydrides of aromatic carboxylic acids such as benzoic, phenylacetic, phenylpropionic or cinnamic acid, or of the halogen, nitro or alkyl derivatives thereof such as chloro-, di- chloro- or trichlorobenzoic acid, mono- or dinitrobenzoic acid, or methyl, ethyl, propyl, n-butyl or isobutyl derivatives of the above aromatic carboxylic acids. Mixed anhydrides of the cited carboxylic acids may likewise be used in accordance with the invention.

According to this invention, it is especially advantageous to employ an acetylation agent for reactions of this kind. Acetylation has proved to be particularly favorable because, apart from cephalosporin C, the desacetyl derivative thereof, that is, desacetyl-cephalosporin C, is present in the culture filtrate, which derivative contains a hydroxy group in 3-position instead of an acetoxy group. This desacetyl compound has a considerably lower microbiological effect than cephalosporin C, and its presence is therefore undesirable in cephalosporin fermentations, but nevertheless inevitable. In the case of an acetylation in accordance with this invention, not only the amino group is acetylated, but also the cited hydroxy group, so that the same reaction product is obtained from both compounds, that is, cephalosporin C and its desacetyl derivative. Such double reaction having a favorable influence on the yield can be carried out, for example, in glacial acetic acid as a solvent. Known acetylation agents such as acetyl chloride, acetic anhydride, ketene and the like can be employed for the acetylation reaction to be carried out according to known methods, for which furthermore the use of catalysts such as pyridine or triethylamine is advantageous.

Under the conditions of the invention, the reaction of cephalosporin C with other amine reagents is facilitated as well. Thus, conversion with good yields to the corresponding urea or thiourea derivatives which generally can be easily crystallized is realizable with isocyanates such as phenyl isocyanate or naphthyl isocyanate, or isothiocyanates such as phenylisothiocyanate.

Formation of Schiff's bases with aldehydes, such as 5-chlorosalicyl aldehyde, as amine reagents is also easy in accordance with this invention. Furthermore, reaction with o-nitrophenylsulfenyl chloride (NPS chloride) to give the NPS derivative is advantageous. This non-polar reaction product may even be extracted from an aqueous solution by means of the selective ethyl acetate solvent, and is thus obtained more easily in a pure state.

The non-polar derivatives of cephalosporin C which can be obtained as has been described above, can be isolated by extraction in known manner from an aqueous solution with a water-immiscible solvent, for example n-butanol, isobutanol, ethyl acetate or methylisobutylketone, preferably butanol. The cephalosporin C derivative can be separated in a the form of a salt from the organic phase in known manner, for example by adding quinoline or isoquinoline. However, such a quinoline/salt precipitation has the disadvantage of not being complete in the case of a cephalosporin C concentration of below 1%, so that the yields are not satisfactory.

Surprisingly, there has been found in accordance with this invention that organic diamines can be used very advantageously instead of quinoline or isoquinoline. As such diamines, unsubstituted or substituted alkyl diamines, may be quite generally employed for the precipitation or alternatively aromatic diamines. Suitable alkyl diamines are especially those of the formula

in which n is an integer of from 4 to 12, preferably 5 to 7, or the derivatives thereof which are obtained for, example, by substituting a hydrogen atom at one or both the nitrogen atoms, or one or more hydrogen atoms of the methylene groups by low weight molecular alkyl, preferably methyl or aryl, especially phenyl. Examples of amines suitable in accordance with the invention are 1,6-diaminoheptane, 2,7-diaminooctane, 2-methyl-hexamethylenediamine, 3-methyl-hexamethylenediamine or N-methyl-hexamethylenediamine, or other N-alkyl derivatives such as N-ethyl or N-propyl or N-phenyl derivatives, furthermore N,N'-dialkyl derivatives such as N,N'-dimethyl-, N,N'-diethyl- or N,N'-dipropyl-hexamethylenediamine. Likewise, the tertiary and quaternary bases, for example of hexamethylenediamine, can be employed. Suitable aromatic diamines which may be used in accordance with this invention are for example diaminobenzenes, especially 1,3-diaminobenzene and the derivatives thereof, preferably methyl or halogen derivatives, especially chlorine derivatives.

When the diamines, especially alkyl diamines having from 5 to 7 carbon atoms, preferably hexamethylenediamine, are used in accordance with this invention as salt forming agents, a selective, nearly complete crystalline precipitation of the cephalosporin C derivative is obtained. In this case, not only the yield is higher than that of the quinoline or isoquinoline salt precipitation, but also the degree of purity of the product.

Extraction from aqueous solution is not required for isolating the non-polar derivatives. Depending on the dissolving power and the undesirable impurities of the culture medium, the non-polar derivatives can be directly precipitated as a free acid, for example by concentration of the solution or addition of other suitable solvents such as ether, ethyl acetate or butyl acetate. This precipitation can alternatively be carried out by adding precipitating agents, for example inorganic ions of heavy metals which form an insoluble salt with cephalosporin C, such as bivalent cobalt, copper, tin or especially zinc ions, or organic bases such as acridine or rivanol.

Generally, it is not required to split off the derivatives or to set free the salts for their further conversion to medicaments, since splitting-off of the acyl radical in known manner to give the 7-amino-cephalosporanoic acid is the generally preferred work-up method. However, in the case where obtaining cephalosporin C is be of interest, the above derivatives can be split off in a manner known from the literature, or the salts can be converted to the free acid according to known methods, for example by treatment with ion exchangers.

The following examples illustrate the invention without limiting its scope thereto.

EXAMPLE 1

180 l of a transparent culture filtrate of a *Cephalosporium acremonium* fermentation are spray-dried within 6 hours. 17 kg of dry culture filtrate are obtained in the form of a light brown powder having 3% of residual moisture and a content of 48 g of cephalosporin C per kg. Furthermore, 10 g of desacetyl-cephalosporin C per kg are present. 3 l of acetic acid are added to 1 kg of this dry culture filtrate and, after 10 minutes agitation, centrifugation is carried out using an Ultra-Turrax$^{(R)}$ apparatus. The undissolved residue is again stirred with 1 l of glacial acetic acid, centrifuged off, and the transparent centrifugation supernatants are united. Subsequently, 350 ml of acetic anhydride and 200 ml of pyridine are added and the whole is left overnight. Thereafter, the batch is concentrated under reduced pressure to about 1 l, and the viscous mass which results is precipitated with 2 l of acetone. The acetylated cephalosporin is present in the precipitate. It is separated, dissolved in 2 l of methanol, and precipiated from the clarified methanol solution by means of a methanolic solution of 100 g of zinc acetate. The precipitate is left overnight. Subsequently the solid phase is separated and dried. 51 g of zinc salt of the acetylated cephalosporin C are present in the 92 g of precipitate.

EXAMPLE 2

3 l of a mixture of methanol and water (9:1) are added to 1 kg of the dry culture filtrate obtained according to Example 1. The whole is thoroughly agitated, filtered, and the undissolved matter is again extracted in the same manner with 2 l of the same mixture. The combined liquid phases (4.5 l) contain 10 g of cephalosporin C per liter. 2 l of this methanolic extract are adjusted to an apparent pH of 8.6 with 40% sodium hydroxide solution and the pH is measured with a pH meter of the company Knick, West Germany. Subsequently, 40 ml of benzoyl chloride and 40% sodium hydroxide solution are added with agitation and within 30 minutes in such a manner that the pH measured remains in a range from 8 to 9, for which purpose 65 ml of the sodium hydroxide solution are required. Agitation is continued for a few minutes, the pH is adjusted to 6 by means of 2 N hydrochloric acid, and the methanol is removed under reduced pressure. The resulting aqueous phase is first degreased with ethyl acetate in an extraction funnel, subsequently adjusted to pH 2.2 and extracted twice with n-butanol. The transparent butanol phases are dried in vacuo by azeotropic distillation and then adjusted to an apparent pH of 5 with 1,6-diaminohexane. The spontaneous crystallization is completed by leaving the batch overnight. The crystalline phase is collected by suction-filtration and dried under reduced pressure. 22 g of the light-colored precipitate contain the N-benzoyl-cephalosporin C-hexamethylenediamine salt in 82% purity.

EXAMPLE 3

2 l of the methanolic extract obtained according to Example 2 are adjusted to a pH of 8.5 as described in Example 2. Subsequently, 60 ml of phenyl-isocyanate are slowly added with agitation and the apparent pH is maintained in a range of from 8 to 9 with sodium hydroxide solution. After 60 minutes reaction time, the pH is adjusted to 6 with 2 N hydrochloric acid, the batch is concentrated in vacuo, extracted with ether, and the separated organic phase is rejected. The aqueous phase is acidified until a pH of 3 is attained and extracted twice with n-butanol. The combined butanol extracts are concentrated in vacuo to 1/5, thus obtaining a crystal pulp which contains 85% of the cephalosporin C used. This crystal pulp is suction-filtered, washed with a small amount of ether, and dried.

EXAMPLE 4

1 g of phosphotungstic acid dissolved in 20 ml of methanol is slowly added with agitation to 1 l of the methanolic solution obtained according to Example 2, thus obtaining a light-colored, voluminous precipitate which is centrifuged off in a laboratory centrifuge at 4,000 g. 300 ml of a 10% methanolic zinc acetate-hydrate solution are subsequently added with agitation to the transparent supernatant containing 9.8 mg of cephalosporin C per ml. A light-colored precipitate is obtained which is inoculated with a few mg of crystalline cephalosporin C-zinc salt in order to complete the precipitation, and then left overnight at 6° C. Subsequently, the precipitate is collected by centrifugation, separated from the liquid phase, washed with acetone and dried in vacuo. The resulting powder contains 9.5 g of cephalosporin C in the form of its zinc salt.

What is claimed is:

1. A method for separating cephalosporin C or a salt or derivative thereof from a culture filtrate or culture solution, which method comprises drying said culture filtrate or culture solution, dissolving the dried filtrate or solution in a solvent other than water, but which may contain water, to form a solution and then
   (a) precipitating cephalosporin C or a salt thereof directly from said solution, or
   (b) reacting the amino group of cephalosporin C to form a derivative thereof, and then isolating said derivative from said solution as the free acid or a salt thereof.

2. A method as in claim 1 wherein said culture filtrate or culture solution is dried by spray drying.

3. A method as in claim 1 wherein said solvent other than water is acetonitrile, dimethyl formamide, a low molecular weight aliphatic alcohol, methyl cellosolve, phenol, pyridine, or trimethyl phosphate.

4. A method as in claim 1 wherein said solvent is formamide.

5. A method as in claim 1 wherein said solvent is glacial acetic acid.

6. A method as in claim 1 wherein said solvent is methanol.

7. A method as in claim 1 wherein cephalosporin C is isolated directly from said solution in the form of a scarcely soluble heavy metal salt thereof.

8. A method as in claim 7 wherein said scarcely soluble heavy metal salt is the zinc salt.

9. A method as in claim 1 wherein a derivative of cephalosporin C is formed by reaction of the amino group thereof with a carboxylic acid halide or a carboxylic acid anhydride.

10. A method as in claim 9 wherein a derivative of cephalosporin C is formed by reaction of the amino group thereof with benzoyl chloride or acetic anhydride.

11. A method as in claim 1 wherein a derivative of cephalosporin C is formed and is then isolated from said solution by direct precipitation.

12. A method as in claim 1 wherein a derivative of cephalosporin C is formed and is then isolated from said solution by transferring the derivative to an aqueous phase, extracting the derivative from said aqueous phase with a water-immiscible solvent, and then precipitating said derivative from said water-immiscible solvent.

13. A method as in claim 12 wherein said derivative is precipitated from said water-immiscible solvent by crystallization of said derivative.

14. A method as in claim 12 wherein said derivative is precipitated from said water-immisicible solvent as the salt thereof with an alkylene diamine or aromatic diamine.

15. A method as in claim 14 wherein said alkylene diamine has the formula $$NH_2-(CH_2)_n-NH_2$$

wherein n is an integer from 4 to 12.

16. A method as in claim 15 wherein n is an integer from 5 to 7.

17. A method as in claim 15 wherein a hydrogen atom on at least one nitrogen atom or at least one methylene hydrogen atom of said alkylene diamine is replaced by lower alkyl or phenyl.

18. A method as in claim 14 wherein said alkylene diamine is 1,6-diaminohexane.

19. A method as in claim 12 wherein said water-immiscible solvent is a butanol, methyl acetate, or methylisobutylketone.

20. A method as in claim 19 wherein said water-immiscible solvent is n-butanol.

* * * * *